United States Patent [19]

Keller

[11] Patent Number: 4,619,986

[45] Date of Patent: Oct. 28, 1986

[54] EPOXY PHTHALONITRILE POLYMERS

[75] Inventor: Teddy M. Keller, Alexandria, Va.

[73] Assignee: The United States of America as represented by the Secretary of the Navy, Washington, D.C.

[21] Appl. No.: 749,705

[22] Filed: Jun. 28, 1985

[51] Int. Cl.⁴ ............................................. C08G 59/40
[52] U.S. Cl. ........................................ 528/99; 528/362
[58] Field of Search ............................. 528/99, 119, 362

[56] References Cited

U.S. PATENT DOCUMENTS

| | | | |
|---|---|---|---|
| 3,301,814 | 1/1967 | Parry | 260/37 |
| 3,903,048 | 9/1975 | Lombardi et al. | 260/47 EN |
| 4,142,034 | 2/1979 | Schroll | 528/120 |
| 4,259,471 | 3/1981 | Keller et al. | 528/9 |
| 4,377,680 | 3/1983 | Sponseller et al. | 528/123 |
| 4,448,940 | 5/1984 | Koyama et al. | 525/504 |
| 4,477,629 | 10/1984 | Hefner | 525/113 |

Primary Examiner—Earl Nielsen
Attorney, Agent, or Firm—Robert F. Beers; Sol Sheinbein; Wendell R. Guffey

[57] ABSTRACT

A bisorthodinitrile monomer having the formula:

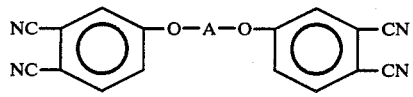

and an epoxy monomer having the formula:

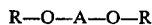

are mixed with or without an amine curing agent and heated to a temperature sufficient to induce polymerization. The resulting epoxy-phthalonitrile copolymer has improved properties relative to the epoxy polymers including higher thermal and oxidative stability, higher glass transition temperature, better shelf life, lower water absorptivity, and better electrical properties. The properties of the epoxy-phthalonitrile copolymer can be varied by varying the epoxy:phthalonitrile ratio.

5 Claims, No Drawings

EPOXY PHTHALONITRILE POLYMERS

BACKGROUND OF THE INVENTION

The present invention pertains generally to polymeric materials and particularly to polymeric materials obtained from the reaction of phthalonitrile and epoxy compounds.

The use of structural adhesives and fiber-reinforced composites in aircraft, guided weapons, ships, and vehicle construction has increased markedly in the last decade and this dramatic growth rate shows every sign of continuing in the future. Conventional epoxy polymers are widely employed as the basis for adhesive compositions and as the matrix material for fiber-reinforced composites. These materials incorporate a latent curing agent and need only heat to initiate cure. When cured, epoxy polymers are highly crosslinked amorphous thermosetting polymers and this structure results in many useful properties such as high modulus, low creep, and good performance between 100°–150° C. Epoxies, however, have several disadvantages especially when being used as a matrix material for composites. Problems include complicated logistics of handling due to low temperature storage requirements for the prepreg with limited shelf life (commonly 6 months at −18° C.), brittleness with poor resistance to crack growth, and engineering reliability attributed to delamination resulting from water penetration into the interface between the matrix material and the reinforcing fiber. In contrast, the prepregs of bisphenol-linked phthalonitrile polymers can be stored indefinitely until needed at room temperature without further reaction. The phthalonitrile polymers show excellent thermal stability when heated in air at 250° C. for extended periods and are self-extinguishing on removal from a high temperature flame. These polymers also have a low affinity for water ($<1.2\%$), which makes them ideal candidates for composites and electronic applications. The phthalonitrile polymers, however, have the disadvantage of requiring higher cure temperatures and longer cure periods relative to the epoxies. In essence, an ideal high performance polymeric system would take advantage of the short cure times and low cure temperatures of the epoxies with the high temperature capability and water resistant of the bisphenol-linked polymers.

Several high performance bisphenol-linked polymers have been previously reported. These polymers can be cured neat or in the presence of organic amines, phenols, or metallic coreactants at 200°–350° C. to afford thermo-setting polymeric materials. Keller, U.S. Pat. No. 4,410,676 discloses a diether-linked phthalonitrile polymer which can withstand temperatures of 200° C. for extended periods of time. U.S. Pat. No. 3,301,814 by Parry discloses a process for curing polyepoxies with phthalocyanines. The phthalocyanines form a "hem-like" structure which can complex metal ions. The complexed phthalocyanine then reacts with the epoxy functional group to form the desired polymer.

Prior disclosures, however, have not shown a process for producing a hydrophobic polymer which can operate at high temperatures and be produced with low cure temperatures and short cure times. A polymeric material is, therefore, needed which can combine the advantages of short cure times and low cure temperatures of the epoxies with the high temperature and water resistant advantages of the phthalonitriles.

SUMMARY OF THE INVENTION

It is, therefore, an object of the present invention to provide a new polymeric system which combines the advantages of the conventional epoxy polymer with those of the bisphenol-linked phthalonitrile polymer.

It is a further object of the present invention to provide a polymer with temperature properties superior to epoxies.

It is another object of the present invention to provide a polymer with a low affinity for water.

It is another object of the present invention to provide a polymer which can be cured at lower temperatures relative to bisphenol-linked phthalonitriles.

It is a further object of the present invention to provide a polymer which is resistant to chemical attack.

These and other objects are achieved by reacting various ratios of bisphenol-linked phthalonitriles and the diglycidyl ether of bisphenol A to produce a polymer having improved physical properties relative to the individual phthalonitrile and/or epoxy polymers.

In the preferred embodiment, equal molar amounts of the diglycidyl ether of bisphenol A (Epon 828) and bisphenol A-linked phthalonitrile are heated to about 200° C. neat or in the presence of a small amount of organic amine to initiate the reaction. The copolymer formed from this invention combines the beneficial properties and characteristics of each homopolymer-Epon 828 and bisphenol A phthalonitrile.

Other objects, advantages, and novel features of the present invention will become apparent from the following detailed description of the invention.

DETAILED DESCRIPTION OF THE INVENTION

The monomers used to practice the present invention are:

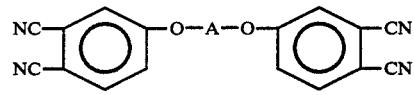

and

wherein A is selected from a group consisting of $-\phi-C_nH_{2n}-\phi-$, $-\phi-SO_2-\phi-$, $-\phi-$, $-C_nH_{2n}-$, and $-\phi-\phi-$, wherein n ranges from 1–4, the phenyl groups are linked at the para or meta positions, and R is selected from the group consisting of linear epoxies having 3–5 carbon atoms.

The polymerization reaction is accomplished by heating the melt of the epoxy-phthalonitrile mixture either neat or in the presence of an organic amine additive and curing at elevated temperatures ($>200°$ C.). The rate of the reaction is substantially enhanced by the amine additive. After a short time which will be dependent on the reactivity and quantity of the amine, the melt starts to darken with a resulting viscosity increase. Quantities of 0–25 percent molar weight of amine to polymerization mixture are generally preferred. The preferred polymerization temperature is from 5° C. above the melting point of the mixture to 30° C. below the decomposition temperature of the polymer, usually between 200°–300° C. Polymerization can be performed in several steps over a series of temperatures.

The preferred polymer is produced by heating the diglycidyl ether of bisphenol A with the phthalonitrile monomer. Generally, about equal molar amounts of the two monomers are mixed and polymerized by heating to about 200°–220° C., neat or in the presence of a small amount of amine. Further heat treatment at higher temperatures for a short time improves the physical properties of the resulting polymer. The new polymer combines the desirable properties and characteristics of the individual epoxy and phthalonitrile polymers. Resorcinol diglycidyl ether and linkage polymers formed from higher homologs of the diglycidyl ether of bisphenol A can also be used to react with the phthalonitrile monomers but the simple diglycidyl ether of bisphenol A is most preferred. If the diglycidyl ether of bisphenol A is used to produce the eopxy-phthalonitrile polymer, the preferred molecular weight range is between 450 and 4000. The most preferred linkage polymer is formed from the diglycidyl ether of bisphenol A in which the repeating unit, n, is greater than 0 and less than or equal to 12 thus producing a linkage polymer having a molecular weight between 450 and 4000.

The overall physical properties of the new polymer will depend on the relative amounts of epoxy, phthalonitrile, and amine used. Although equimolar amounts of the phthalonitrile and epoxy monomers are most preferred, the physical properties of the resulting polymer can be varied by varying the ratio of phthalonitrile monomer to epoxy monomer. Even a trace amount of one monomer reacted with an excess of the other monomer will give new characteristic properties to the resulting polymer. Mixtures of mole ratios of 20:1 epoxy-phthalonitrile and phthalonitrile-epoxy diminish the water uptake and Tg values of the resulting polymer. Mole ratios of 5:1 produce dramatic changes in the properties of the polymer as compared to the epoxy or phthalonitrile polymer alone. In all cases, the thermo-oxidative stability is enhanced with a resulting higher char yield relative to the epoxy cured with an amine. Moreover, there is an improvement in the equilibrium water uptake of the epoxy-phthalonitrile polymers (<1.5%) relative to the epoxy polymer (>3.5%). There is an enhancement in the glass transition temperatures ($T_g$) relative to the epoxy polymer used whose value is again dependent on the relative amounts of each reactant, with higher ratios of phthalonitrile to epoxy favoring higher Tg's. The major improvements of the new polymer relative to the phthalonitrile polymer is the processing or polymerization conditions. Lower temperatures are required for the polymerization reaction pertaining to the reaction invention. The major sacrifice is in the thermal properties with said properties less than for the amine-cured phthalonitrile polymer.

Aromatic diamines, e.g., m and p-phenylenediamine, 4,4'-methylenedianiline, 4-aminophenyl sulfone, 4-aminophenyl ether and 4,4'-(p-phenylenedioxy) dianiline are preferred as curing additives due to their commercial availability and to their thermal stability at the elevated temperatures necessary for polymerization. Aliphatic amines are less desirable due to a sacrifice in the thermooxidative stability. Any amine (primary, secondary, or tertiary amine) will enhance the cure rate to a certain degree if it does not vaporize or decompose below the polymerization temperature.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

Bisphenol A phthalonitrile (0.77 g, 1.6 mmol) and Epon 828 (0.51 g, 1.5 mmol) were weighed into an aluminum planchet, then placed on a preheated hot plate at 190° C. and heated with stirring until homogeneity occurred. The mixture was degassed while still in the melt at reduced pressure. At this time, 4,4'-methylenedianiline (0.04 g, 0.2 mmol) was added to the mixture. The initially clear composition started to darken almost immediately with a detected increase in viscosity. The sample was placed in an oven preheated at 200° C. After 3 hours, the sample had solidified and had taken on the same color as the phthalonitrile polymer (dark green). The sample was heated at 200° C. for 8 hours and postcured at 270° C. for 2 hours. Even through the planchet had been sprayed with releasing agent, the cured polymer adhered strongly to the aluminum upon cooling. Moreover, the epoxy-phthalonitrile polymer appeared to be less brittle than either bisphenol A phthalonitrile or Epon 828 cured individually with 4,4'-methylenedianiline.

A second sample containing bisphenol A phthalonitrile (0.77 g, 1.6 mmol), Epon 828 (0.51 g, 1.5 mmol) and 4,4'-methylenedianiline (0.04 g, 2 mmol) was prepared as above and used for a water absorptivity study. The polymeric composition has a low equilibrium water uptake (1.4%) after 2 years immersion.

EXAMPLE II

Bisphenol A phthalonitrile (0.58 g, 1.21 mmol) and Epon 828 (0.76 g, 2.24 mmol) were weighed into an aluminum planchet and heated to 200° C. on a hot plate specially designed into a desiccator and degassed at reduced pressure. At this time, 4,4'-methylenedianiline (0.02 g, 0.1 mmol) was added and thoroughly mixed by stirring. The sample was then placed in a preheated oven at 200° C. and heated for 24 hours. Sometime during this heat treatment, the sample solidified. The sample was postcured at 260° C. for 2 hours. The dark polymer appeared to be less brittle than the individual polymers cured with 4,4'-methylenedianiline.

A sample prepared in a similiar manner was used for a water absorptivity study. After 2 years immersion, the polymer has a equilibrium water uptake value of 1.2%.

EXAMPLE III

Bisphenol A phthalonitrile (0.59 g, 1.05 mmol) and Epon 828 (0.16 g, 0.47 mmol) were weighed into an aluminum planchet and heated to 210° C. on a hot plate specially designed into a desiccator and degassed at reduced pressure. At this time, 4,4'-methylenedianiline (0.08 g, 0.04 mmol) was added and thoroughly mixed by stirring. The sample was then placed in an oven preheated to 220° C. and heated overnight. The polymer was then postcured at 270° C. for 2 hours. A sample prepared in a similar manner showed an equilibrium water uptake of 1.4% after 2 years immersion.

EXAMPLE IV

Biphenol phthalonitrile (0.70 g, 1.6 mmol), prepared from p,p'-biphenol and 4-nitrophthalonitrile, and Epon 828 (0.51 g, 1.5 mmol) were weighed into an aluminum planchet and heated to 220° C. on a hot plate specially designed into a desiccator and degassed at reduced pressure. To the melt was added 4,4'-methylenedianiline (0.01 g, 0.05 mmol). After thoroughly mixing by stirring, the sample was placed in a preheated oven at 220° C. After 5 hours, the sample had solidified and was heated for an additional 12 hours. The sample was postcured at 270° C. for 2 hours.

EXAMPLE V

Bisphenol A phthalonitrile (0.77 g, 1.6 mmol) and Epon 828 (0.51 g, 1.5 mmol) were weighed into an aluminum planchet, melted at 210° C. and degassed at reduced pressure. 4-Aminophenyl sulfone (0.05 g, 0.2 mmol) was added and thoroughly mixed by stirring. The sample was then placed in a preheated oven at 210° C. and heated for 24 hours resulting in solidification. The polymer was then postcured at 270° C. for 2 hours.

EXAMPLE VI

Bisphenol A phthalonitrile (0.77 g, 1.6 mmol) and Epon 28 (0.53 g, 1.6 mmol) were placed in an aluminum planchet, heated to a melt at 210° C. and degassed at room temperature. After 5 hours of heating at 210° C., it was observed that a tint of brown was forming in the sample. After heating at 210° C. for 24 hours, the sample has solidified. Cure time is slower than when an amine is present. The sample was postcured at 270° C. for 2 hours.

The new polymer of this invention exhibits the following advantages over the conventional epoxy polymer based on bisphenol A (Epon 828): Higher thermal and oxidative stability, higher glass transitic,n temperature, better shelf life, lower water absorptivity, and better electrical properties. The epoxy-phthalonitrile copolymer could, therefore, be used for coatings, plastics, and adhesives, high performance composites, composite repairs, and easily processable dielectric insulators in a variety of applications in the electronic industry, e.g., in the production of semiconductor devices.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A process for producing an epoxy-phthalonitrile copolymer, which comprises:

mixing amounts of an epoxy monomer having the formula,

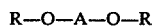

wherein A is selected from a group consisting of $-\phi-C_nH_{2n}-\phi-$, $-\phi-SO_2-\phi-$, $-\phi-$, $-C_nH_{2n}-$, and $-\phi-\phi-$, wherein n ranges from 1–4, wherein the phenyl groups are linked at the para or meta positions, and wherein R is selected from the group consisting of linear epoxides having 3–5 carbon atoms; with a phthalonitrile monomer having the formula,

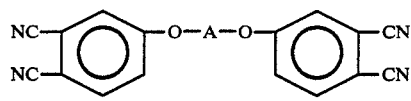

wherein A is selected from a group consisting of $-\phi-C_nH_{2n}-\phi-$, $-\phi-SO_2-\phi-$, $-\phi-$, $-C_nH_{2n}-$, and $-\phi-\phi-$, wherein n ranges from 1–4, wherein the phenyl groups are linked at the para or meta positions, said epoxy and phthalonitrile monomers being mixed in a molar ratio ranging from about 20:1 epoxy:phthalonitrile to about 20:1 phthalonitrile:epoxy; and heating the epoxy-phthalonitrile mixture in the presence of an amine additive selected from the group consisting of m-phenylenediamine, p-phenylenediamine, 4,4'-methylenedianiline, 4-aminophenyl sulfone, 4-aminophenyl ether and 4,4'-(p-phenylenedioxy)dianiline to a temperature sufficient to polymerize said mixture, said temperature being between the polymerization mixture melting point and decomposition temperature.

2. The process of claim 1 wherein said monomers are mixed in a molar ratio ranging from about 5:1 epoxy:phthalonitrile to about 5:1 phthalonitrile:epoxy.

3. The process of claim 2 wherein said epoxy and phthalonitrile monomers are mixed in about equimolar amounts.

4. The process of claim 3 wherein said epoxy monomer is selected from the group consisting of the diglycidyl ether of bisphenol A (Epon 828), linkage polymers produced from diglycidyl ether of bisphenol A having a repeating unit ranging from 1–12, and resorcinol diglycidyl ether.

5. The process of claim 4 wherein said mixture is heated to a temperature between 200°–300° C.

* * * * *